United States Patent [19]

Cipullo

[11] Patent Number: 5,786,522
[45] Date of Patent: Jul. 28, 1998

[54] MANUFACTURE OF BISPHENOL-A

[75] Inventor: Michael J. Cipullo, Prattville, Ala.

[73] Assignee: General Electric Company, Pittsfield, Mass.

[21] Appl. No.: 712,929

[22] Filed: Sep. 13, 1996

[51] Int. Cl.$^6$ ........................................ C07C 37/84
[52] U.S. Cl. ........................................ 568/724; 568/727
[58] Field of Search ........................................ 568/724, 727

[56] References Cited

U.S. PATENT DOCUMENTS

| | | |
|---|---|---|
| 3,326,986 | 6/1967 | Dugan . |
| 4,294,995 | 10/1981 | Faler . |
| 4,327,229 | 4/1982 | Mendiratta et al. ........... 568/728 |
| 4,346,247 | 8/1982 | Faler . |
| 4,365,099 | 12/1982 | Faler et al. . |
| 4,375,567 | 3/1983 | Faler . |
| 4,396,728 | 8/1983 | Faler . |
| 4,584,416 | 4/1986 | Pressman . |
| 4,590,303 | 5/1986 | Mendiratta . |
| 4,847,433 | 7/1989 | Kissinger . |
| 4,876,391 | 10/1989 | Kissinger . |
| 4,876,395 | 10/1989 | Kissinger . |
| 5,075,511 | 12/1991 | Li . |
| 5,105,027 | 4/1992 | Desmurs et al. . |
| 5,146,007 | 9/1992 | Cipullo . |
| 5,210,329 | 5/1993 | Gomes de Matos et al. . |
| 5,243,093 | 9/1993 | Kissinger et al. . |
| 5,315,042 | 5/1994 | Cipullo . |
| 5,362,900 | 11/1994 | Kissinger . |
| 5,399,789 | 3/1995 | Cipullo et al. . |
| 5,405,933 | 4/1995 | Sakashita et al. . |
| 5,414,152 | 5/1995 | Cipullo . |
| 5,434,316 | 7/1995 | Kissinger . |
| 5,475,152 | 12/1995 | Kissinger et al. . |

*Primary Examiner*—Gary Geist
*Assistant Examiner*—Sreeni Padmanabhan

[57] ABSTRACT

An integrated process for the preparation and recovery of BPA in pure form utilizes a series of steps to crystallize pure BPA of improved color stability and recycle separated impurities to improve overall yields. The principal impurity recycled to the process is o,p-BPA which functions as a color stabilizer in the product and in polycarbonate resins prepared from the BPA.

8 Claims, 1 Drawing Sheet

MANUFACTURE OF BISPHENOL-A

BACKGROUND OF THE INVENTION

1. Field of the Invention

The invention relates to a process for the manufacture of bisphenol-A.

2. Brief Description of Related Art

The dihydric phenol 2,2bis(p-hydroxyphenyl) propane (commonly referred to as "bisphenol-A", "BPA" or "pp-BPA") is commercially prepared by condensing 2 moles of phenol with a mole of acetone in the presence of an acid catalyst The phenol is present in the reaction in a molar excess of the stoichiometric requirement. During the condensation, a number of by-products such as isomeric forms of the BPA are formed which are considered contaminants of the desired product, BPA. These contaminants are carried in the product stream from the condensation reaction zone, with water, trace quantities of acidic materials derived from the catalyst, unreacted phenol and unreacted acetone. Currently, the purification of the desired product BPA is a costly and multi-step procedure.

A principal use of BPA is as a monomer for polymerization to obtain polycarbonate and polyestercarbonate resins. For many of these polymeric resins, color, lack of color and stability of color is important to the end use, such as transparent lenses. Recently, it has been found that one of the BPA isomers, 2-(4-hydroxy-phenyl)-2-(2-hydroxyphenyl) propane, also referred to as o,p-BPA, which occurs as a contaminant in the commercial preparation described above, acts as a color stabilizer when present in resins prepared by polymerization of BPA. This recent work indicates that o,p-BPA concentrations of at least about 100 ppm, in the monomer BPA, upon polymerization, can produce polycarbonate resins with improved color (as measured by the Yellowness Index).

The present invention takes advantage of the recent discovery described above, by modifying the preparation of the monomer BPA to increase the o,p-BPA contaminant content of the product, and thereby its value as a color stable polycarbonate resin precursor. The advantage of the improved method of the invention resides in the avoidance of increasing concentrations of other contaminants associated with the preparation of BPA such as BPX-II, BPX-I, dimers and the like.

There are two commercially important processes for the synthesis of BPA currently in use. One process is sometimes called the "HCL" process, in reference to the acidic catalyst employed (hydrogen chloride).

The second commercial synthesis reaction involves the use of an active ion exchange catalyst and is sometimes called the "IER" process. Both synthesis involve passing phenol, acetone and recycled by-products through a reactor containing an acid catalyst followed by a BPA purification scheme. The "IER process" can be done in one of two ways; first, until essentially complete acetone depletion; second, and most desirable, is "partial acetone conversion". This technology is described in U.S. Pat. No. 5,315,042 which is hereby incorporated herein by reference thereto. The BPA reaction can be optionally promoted by the presence of a free mercaptan such as 3-mercaptopropionic acid, or use a promoter which is chemically or covalently bonded to the EIR resin, or use no promoter. These resins are generally well known compositions as are methods of their preparation; see for example the preparative procedures described in U.S. Pat. No. 3,037,052 which is hereby incorporated herein by reference thereto.

The IER process reaction effluent contains unreacted acetone, phenol, BPA, an adduct of BPA and phenol and isomeric by-products of BPA, along with the promoter (when present). This effluent (or the HCl process reaction effluent) may be fed to a stripping operation which removes the water of reaction, residual acetone and phenol.

Representative of more detailed descriptions of the above processes for condensing phenol with acetone to obtain BPA are those found in the U.S. Pat. Nos. 4,346,247; 4,396,728; 4,400,555; 4,424,283; 4,584,416; 4,766,254 and 4,847,433; all of which are incorporated herein by reference thereto. The factor shared by all of these known methods and processes is the need to purify and recover the product BPA in steps subsequent to the condensation reaction. Another sub process often present in either the HCl or IER BPA manufacturing process is a "recovery process" used to recover useful materials from the purge streams. This can be done by catalytic cracking of the stream to produce and recover phenol (for example as described by U.S. Pat. No. 4,131,749), by adduct crystallization (U.S. Pat. No. 5,210, 329) or by distillation (see for example U.S. Pat. No. 5,300,702 or European Patent (U.K.) 055,251A issued Sep. 13, 1995).

The present invention is a modified process for producing purified BPA in a fully integrated commercial process beginning with the condensation reaction product.

SUMMARY OF THE INVENTION

The invention comprises, a process for the manufacture of BPA, which comprises;

(a) condensing phenol with acetone in a reaction zone, in the presence of a stoichiometric excess of phenol and a catalytic proportion of an acid catalyst, whereby a reaction zone effluent is obtained comprising unreacted phenol, unreacted acetone, water, tars and by-product isomers of BPA including o,p-BPA in admixture with the desired BPA adducted with phenol;

(b) precipitating crystals of the BPA/phenol adduct from the effluent, leaving a mother liquor;

(c) purging at least a portion of the mother liquor from the process;

(d) recrystallizing the separated crystals of BPA/phenol adduct;

(e) dewatering and distilling the purge to obtain a lights fraction containing o,p-BPA; and (f) adding at least a portion of the lights fraction to the BPA/phenol adduct crystals separated from the mother liquor before the recrystallization of step (d) above, to adjust the op-bisphenol content thereof to a color stabilizing proportion

BRIEF DESCRIPTION OF THE DRAWING

The accompanying drawing is a block diagram showing an embodiment process of the invention.

DETAILED DESCRIPTION OF THE PREFERRED EMBODIMENT OF THE INVENTION

Figure 1:
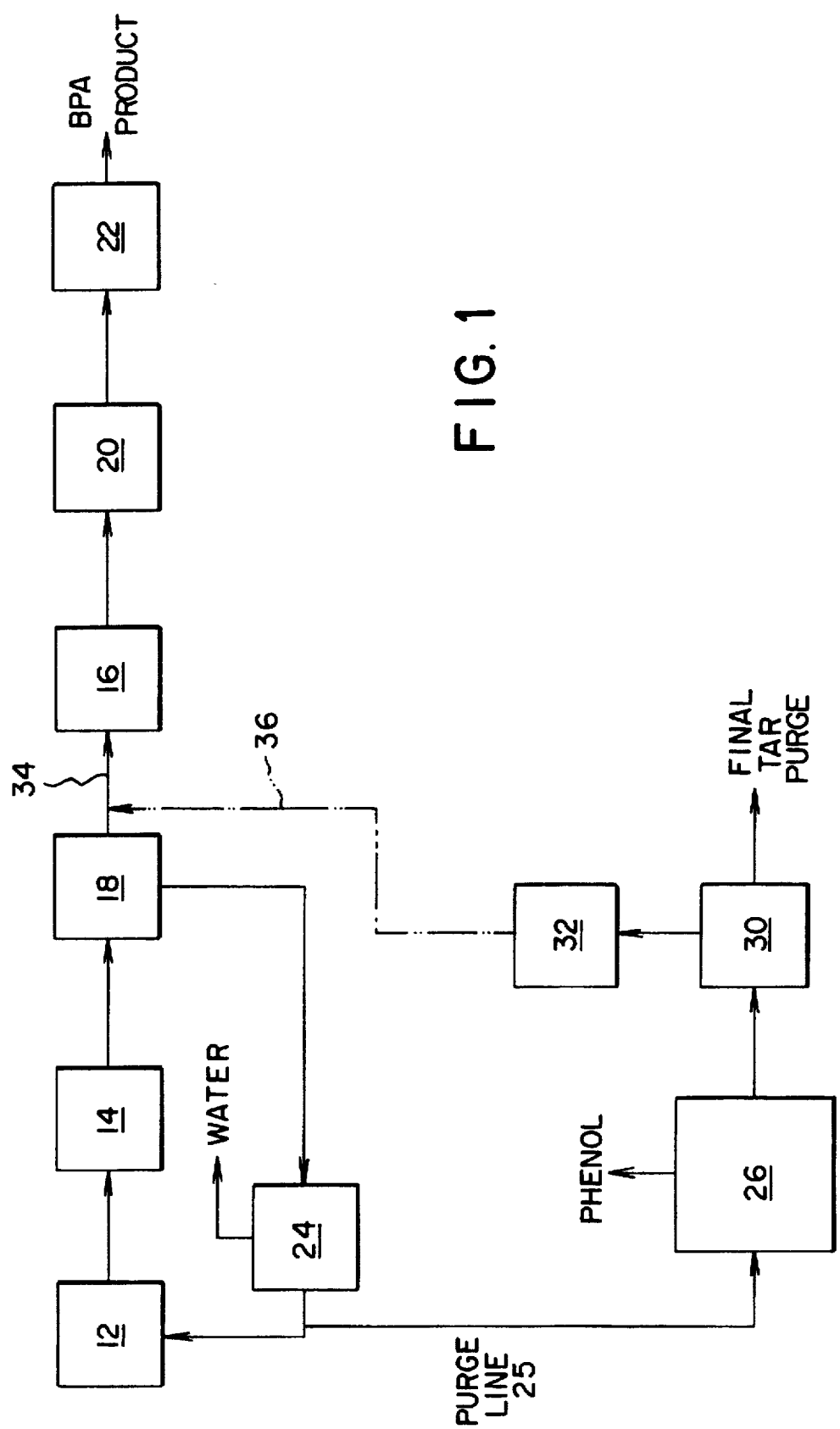

The commercially important processes for preparing BPA comprise condensation of 2 moles of phenol with a mole of acetone in the presence of an acid catalyst and a stoichiometric excess of the phenol reactant; see for example the U.S. Patents referred to above in the Brief Description of the Related Art. As shown in the accompanying drawing, to illustrate an embodiment process of the present invention, this reaction is the starting point of the present process. Any of the previously described reaction conditions and catalysts can be employed to obtain the reaction zone effluent for continued handling according to the process of the invention.

Preferred is the condensation procedure of U.S. Pat. No. 5,315,042, incorporated herein by reference thereto.

As depicted in the accompanying drawing, the condensation is carried out conventionally in a reaction zone (12). The reaction effluent containing crude BPA phenol, isomers of BPA (including 0 to 5 percent by weight of o,p-BPA), water, acetone and other reaction by-products is conventionally carried to a multiple stage crystallization where at least one crystallization (unit 14) and one recrystallization (unit 16) are performed, to precipitate BPA/phenol adduct crystals. Solids/liquid separation (filtration or centrifugation) is carried out after each precipitation of crystals in units 18, 20 to separate the mother liquor. After the crystallizations and filtrations, the purified adduct is stripped of phenol in phenol recovery unit 22, to obtain a BPA product The molten pure BPA product from recovery unit 22 can be recovered in a variety of forms including "flakes" by solidifying the melt on a cooled rotating drum, or as, "prills" from a prilling operation.

The first mother liquor separated from the precipitated BPA/phenol adduct crystals is normally de-watered in unit 24 and recycled back to reaction zone 12 for recovery of some of the phenol and BPA values contained in the liquor. Alternatively, the water (and unreacted acetone, if present) can be removed before adduct crystallization. This first mother liquor generally contains in addition to water high proportions of o,p-BPA which will isomerize in the reaction zone 12 in subsequent reactions. To avoid build-up of undesired contaminants to BPA, a remaining portion of the dewatered first mother liquor has heretofore been purged in a purge line 25 from the process line described above to a recovery process to remove a first fraction which comprises phenol, (stripper 26). The phenol stripped product of stripper 26 is then processed to separate p,p-BPA, chroman and other valuable by-products (lights) of the BPA synthesis, by distillation in distillation column 30 (or in multiple columns). This lights fraction collected in vessel 32 contains a high proportion of o,p-BPA which can be used to adjust the o,p-BPA content of the first crystallization of BPA/phenol adduct obtained from unit 18. The adjustment is made by adding at least a portion of the lights distillate from vessel 32 to the first adduct crystals prior to unit 16 in an amount sufficient to provide a color stabilizing proportion. A color stabilizing proportion is generally within the range of from about 0.01 to about 3% by weight of p,p-BPA, preferably from 0.01 to 0.3% by weight, more preferably from about 0.015 to about 0.1% by weight and still more preferably from about 0.02 to about 0.08% by weight. The addition to the product of unit 18 prior to passage through unit 16 is in the process line 34 via conduit 36 (shown by a broken line).

The distilled phenol from stripper 26 which is in admixture with some water and some acetone, can be recovered in pure, substantially anhydrous state for further condensations in reaction zone (12) by further distillation, using known procedures.

The following example describes the manner and the process of making and using the invention and sets forth the best mode contemplated by the inventor for carrying out the invention but is not to be construed as limiting.

EXAMPLE

A feed solution was obtained (residual crystallization liquor) from a commercial production of BPA following the first crystallization and separation of BPA/phenol adduct from the condensation reactor effluent. Analysis of an aliquot of the feed solution showed components as set forth in Table 1, below.

|  | Table 1 Wt % | Table 2 Wt % | Table 3 Wt % | Table 4 Wt % |
| --- | --- | --- | --- | --- |
| Phenol | 67.81 | 0.4 | 0.01 | 0.01 |
| pp-BPA | 25.81 | 23.3 | 99.91 | 99.94 |
| op-BPA | 2.38 | 40.3 | 0.041 | 0.007 |
| Dimers | 2.04 | 2.0 | 0.000 | 0.000 |
| Chroman | 0.61 | 22.3 | 0.000 | 0.000 |
| Spiro | 0.25 | 0.1 | 0.000 | 0.000 |
| BPX-I | 0.56 | 0.0 | 0.001 | 0.002 |
| BPX-II | 0.54 | 1.0 | 0.02 | 0.028 |

The mother liquor solution was dewatered, filtered and distilled at a temperature of circa 410° F. under a reduced pressure of 35 mm Hg 35 absolute to remove phenol. A second distillation at a temperature of about 450°–470° F. under a pressure of about </mm yielded a lights fraction, which upon analysis showed a content as set forth in Table 2, above.

A portion of the "lights" fraction was added back to the BPA/pphenol adduct crystals separated, in the form of a melt and recrystallization carried out. Analysis of the recrystallized product following phenol desorption is set forth in Table 3, above. Table 4 provides typical composition as without the benefit of this invention (i.e. a recrystallization of the Table 1 material without addition of the material in Table 2.

Those skilled in the art will appreciate that the amount of increase of op-BPA in the product will depend on the composition of the first adduct material, the distillation conditions chosen, resulting composition of the lights and the quantity of the lights that one chooses to send to the second crystallization operation. This invention provides a means to recover and reuse useful light boiling materials (op-BPA, pp-BPA) and remove the "heavies" (BPX-I, BPX-II, Dimers, etc.) The "heavy" by-products can be a source of color, induce polymer branching, or negatively impact other physical properties. The composition of the light stream can be modified to accommodate a wide variety of by-product compositions depending on the concentrations desired. The level of op-BPA in the light stream can range from about 10% by weight to about 80% by weight. Under most usual operating conditions the light stream will have an op-BPA content of from about 20% by weight to about 70% by weight The concept is also applicable to other commercial BPA processes employing multi-stage purification systems, such as melt crystallization (as described, for example, in U.S. Pat. No. 5,243,093). In this case, a process stream rich in o,p-BPA can be added to one of the crystallization stages in an amount that enriches the product o,p-BPA concentration without significantly affecting the concentrations of other product contaminants.

The U.S. Patents mentioned herein are hereby incorporated herein by reference thereto.

What is claimed is:

1. A process for the manufacture of BPA, which comprises; condensing phenol with acetone in a reaction zone, in the presence of a stoichiometric excess of phenol and a catalytic proportion of an acid catalyst, whereby a reaction zone effluent is obtained (a) comprising unreacted phenol, unreacted acetone, water, tars and by-product isomers of BPA including o,p-BPA;

(b) precipitating crystals of the p,p-BPA/phenol adduct from the effluent, leaving a mother liquor;

(c) purging at least a portion of the mother liquor from the process;

(d) recrystallizing the separated crystals of p,p-BPA/phenol adduct;

(e) dewatering and distilling the purge or by-product stream to obtain a lights fraction containing o,p-BPA; and (f) adding at least a portion of the lights fraction to the p,p-BPA/phenol adduct separated from the mother liquor before the recrystallization of step (d) above, to adjust the o,p-BPA content thereof to a color-stabilizing proportion in the amount of from about 0.01 to about 3% by weight of p,p-BPA.

2. A process for the manufacture of BPA, which comprises;

(a) condensing phenol with acetone in a reaction zone, in the presence of a stoichiometric excess of phenol and a catalytic proportion of an acid catalyst, whereby a reaction zone effluent is obtained comprising unreacted phenol, unreacted acetone, water, tars and by-product isomers of BPA including o,p-BPA;

(b) precipitating crystals of the p,p-BPA/phenol adduct from the effluent, leaving a mother liquor;

(c) removing water from the mother liquor or reactor and effluent before crystallization;

(d) recycling a first portion of the dewatered mother liquor to the reaction zone for further reaction;

(e) purging a second portion of the dewatered mother liquor from the process;

(f) recrystallizing the separated crystals of p,p-BPA/phenol adduct;

(g) removing phenol from the recrystallized adduct;

(h) stripping phenol from the purged second portion of dewatered mother liquor;

(i) distilling the phenol stripped purge to remove a lights fraction containing o,p-BPA; and (j) adding at least a portion of the lights fraction to the p,p-BPA/phenol adduct crystals separated from the mother liquor before the recrystallization of step (f) above, to adjust the o,p-BPA content thereof to a color-stabilizing proportion in the amount of from about 0.01 to about 3% by weight of p,p-BPA.

3. The process of claim 2 wherein the o,p-BPA content is in the amount of from about 0.01 to 0.3% by weight of p,p-BPA.

4. The process of claim 2 wherein the o,p-BPA content is in the amount of from about 0.015 to about 0.1% by weight of p,p-BPA.

5. The process of claim 2 wherein the o,p-BPA content is in the amount of from about 0.02 to about 0.08% by weight of p,p-BPA.

6. The process of claim 1 wherein the o,p-BPA content is in the amount of from about 0.01 to 0.3% by weight of p,p-BPA.

7. The process of claim 1 wherein the o,p-BPA content is in the amount of from about 0.015 to about 0.1% by weight of p,p-BPA.

8. The process of claim 1 wherein the o,p-BPA content is in the amount of from about 0.02 to about 0.08% by weight of p,p-BPA.

* * * * *